(12) United States Patent
Walker et al.

(10) Patent No.: US 7,174,893 B2
(45) Date of Patent: *Feb. 13, 2007

(54) MASK WITH ANTI-ASPHYXIA VALVE

(75) Inventors: Adrienne Mary Claire Walker, Blackburn South (AU); Geoffrey Crumblin, Baulkham Hills (AU); Gregory Scott Smart, Randwick (AU); Michael Kassipillai Gunaratnam, Marsfield (AU); Philip Rodney Kwok, Chatswood (AU); Perry D. Lithgow, Glenwood (AU)

(73) Assignee: ResMed Limited, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 11/285,077

(22) Filed: Nov. 23, 2005

(65) Prior Publication Data

US 2006/0076017 A1 Apr. 13, 2006

Related U.S. Application Data

(60) Continuation of application No. 09/985,458, filed on Nov. 2, 2001, now Pat. No. 7,089,939, which is a division of application No. 09/498,705, filed on Feb. 7, 2000, now Pat. No. 6,491,034.

(30) Foreign Application Priority Data

Feb. 9, 1999 (AU) .................... PP 8550

(51) Int. Cl.
*A62B 18/02* (2006.01)
*A62B 18/10* (2006.01)
*A62B 9/02* (2006.01)

(52) U.S. Cl. .................... 128/206.21; 128/207.12; 128/205.24

(58) Field of Classification Search ........... 128/204.18, 128/205.24, 205.25, 202.27, 206.12, 206.15, 128/206.16, 206.21, 206.26, 207.12, 912, 128/206.28; 285/81, 86, 305

See application file for complete search history.

(56) References Cited

U.S. PATENT DOCUMENTS

| | | | |
|---|---|---|---|
| 812,706 | A | 2/1906 | Warbasse |
| 1,653,572 | A | 12/1927 | Jackson |
| 2,029,129 | A | 1/1936 | Schwaritz |
| 2,359,506 | A | 10/1944 | Battley et al |
| 2,371,965 | A | 3/1945 | Lehmberg |

(Continued)

FOREIGN PATENT DOCUMENTS

DE 297 21 766 U1 3/1998

(Continued)

*Primary Examiner*—Teena Mitchell
(74) *Attorney, Agent, or Firm*—Nixon & Vanderhye P.C.

(57) ABSTRACT

An anti-asphyxia valve includes at least one flap having a first portion adapted for mounting to the housing and a second portion adapted to flex between a first open position allowing gas to pass from the patient side to the housing interior through the at least one port, and from the blower side through the at least one port, to atmosphere when a difference in gas pressure in the housing interior and atmosphere is below a predetermined operating threshold, and a second forcibly closed position substantially occluding the at least one port when the difference in gas pressure between the housing interior and atmosphere is substantially equal to or above the operating threshold.

32 Claims, 14 Drawing Sheets

U.S. PATENT DOCUMENTS

| | | | |
|---|---|---|---|
| 2,893,387 A | 7/1959 | Gongoll et al. | |
| 2,931,356 A | 4/1960 | Schwarz | |
| 3,189,027 A | 6/1965 | Bartlett, Jr. | |
| 3,474,783 A | 10/1969 | Ulmann | |
| 3,824,999 A | 7/1974 | King | |
| 4,064,875 A | 12/1977 | Cramer et al. | |
| 4,111,197 A | 9/1978 | Warncke et al. | |
| 4,121,580 A | 10/1978 | Fabish | |
| 4,164,942 A | 8/1979 | Beard et al. | |
| 4,226,234 A | 10/1980 | Gunderson | |
| 4,274,404 A | 6/1981 | Molzan et al. | |
| 4,494,538 A | 1/1985 | Ansite | |
| 4,506,665 A | 3/1985 | Andrews et al. | |
| 4,580,556 A | 4/1986 | Kondur | |
| 4,606,340 A | 8/1986 | Ansite | |
| 4,622,964 A | 11/1986 | Flynn | |
| 4,794,921 A | 1/1989 | Lindkvist | |
| 4,807,617 A | 2/1989 | Nesti | |
| 4,809,692 A | 3/1989 | Nowacki et al. | |
| 4,841,953 A | 6/1989 | Dodrill | |
| 4,870,963 A | 10/1989 | Carter | |
| 4,898,174 A | 2/1990 | Fangrow, Jr. | |
| 4,974,586 A | 12/1990 | Wandel et al. | |
| 4,997,217 A | 3/1991 | Kunze | |
| 5,005,568 A | 4/1991 | Loescher et al. | |
| 5,253,641 A | 10/1993 | Choate | |
| 5,311,862 A | 5/1994 | Blasdell et al. | |
| 5,398,673 A | 3/1995 | Lambert | |
| 5,438,981 A | 8/1995 | Starr et al. | |
| 5,501,214 A | 3/1996 | Sabo | |
| 5,645,049 A | 7/1997 | Foley et al. | |
| 5,647,355 A | 7/1997 | Starr et al. | |
| 5,647,357 A * | 7/1997 | Barnett et al. | 128/206.24 |
| 5,676,133 A | 10/1997 | Hinckle et al. | |
| 5,709,204 A | 1/1998 | Lester | |
| 5,724,965 A | 3/1998 | Handke et al. | |
| 5,839,436 A | 11/1998 | Fangrow et al. | |
| 5,878,743 A * | 3/1999 | Zdrojkowski et al. | 128/204.23 |
| 5,896,857 A | 4/1999 | Hely et al. | |
| 5,921,239 A * | 7/1999 | McCall et al. | 128/205.25 |
| 5,937,851 A | 8/1999 | Serowski et al. | |
| 6,189,532 B1 | 2/2001 | Hely et al. | |
| 6,192,886 B1 | 2/2001 | Rudolph | |
| 6,196,223 B1 | 3/2001 | Belfer et al. | |
| 6,412,487 B1 | 7/2002 | Gunaratnam et al. | |
| 6,491,034 B1 | 12/2002 | Gunaratnam et al. | |
| 6,615,832 B1 | 9/2003 | Chen | |
| 2002/0023650 A1 | 2/2002 | Gunaratnam et al. | |
| 2004/0255948 A1* | 12/2004 | Smith et al. | 128/206.15 |

FOREIGN PATENT DOCUMENTS

| | | |
|---|---|---|
| EP | 1 027 905 A3 | 8/2000 |
| FR | 2 691 906 | 12/1993 |
| WO | WO 80/01645 | 8/1980 |
| WO | WO 98/26830 | 6/1998 |
| WO | WO 98/48878 | 11/1998 |
| WO | WO 00/38772 | 7/2000 |

* cited by examiner

MASK WITH ANTI-ASPHYXIA VALVE

CROSS REFERENCE TO RELATED APPLICATIONS

This is a Continuation of U.S. application Ser. No. 09/985,458, filed Nov. 2, 2001, now U.S. Pat. No. 7,089,939, which is a Divisional of U.S. application Ser. No. 09/498,705, filed on Feb. 7, 2000, now U.S. Pat. No. 6,491,034, each incorporated herein by reference in its entirety.

FIELD OF THE INVENTION

This invention relates to improvements in patient gas delivery apparatus of the kind used in the analysis and treatment of respiratory disorders. The invention will be described with particular reference to patient gas delivery apparatus used in the treatment of respiratory disorders such as Obstructive Sleep Apnea (OSA) but it is not intended to be limited thereto.

The present invention also relates to an anti-asphyxia valve. The valve has been developed primarily for use between a patient and means (e.g., a blower or respirator) to deliver a breathable gas to the patient, such as is used in the Continuous Positive Airway Pressure (CPAP) treatment of Obstructive Sleep Apnea (OSA), and will be described hereinafter with reference to this application. The valve is also suitable for use in other gas delivery systems, such as those used in assisted respiration and Non-Invasive Positive Pressure Ventilation (NIPPV).

BACKGROUND OF THE INVENTION

Patient gas delivery apparatus of the kind having a mask worn by a patient and a gas delivery conduit attached to the mask are commonly used in the analysis and treatment of respiratory disorders. The gas conduit delivers a gas under pressure to the patient. It is necessary that the gas conduit is detachable from the mask to facilitate cleaning.

Patient gas delivery apparatus typically includes at a minimum, a gas delivery conduit and a nose or full face mask. In some cases it is a clinical requirement that additional components be included, such as means for $CO_2$ washout, for example, vents, anti-asphyxia valves and the like. In some cases, these additional components must be assembled in between the gas delivery conduit and the mask. Problems with prior art assemblies include:

(a) They may be inadvertently assembled without the additional components (b) They may be incorrectly assembled, for example, incorrectly aligned (c) During the course of treatment, the patient may inadvertently remove or dismantle the assembly and incorrectly reassemble it.

Further, known mask cushions are usually molded from a relatively soft, resilient, elastic material and they are shaped during manufacture to match the facial contours of an average intended wearer. However, a problem with the known types of masks is that, because individuals vary so much from the average, the masks must be forced against their inherent resiliency to deform and so adapt to the shapes of the users in order to avoid gas leakage. This requires that the masks be secured firmly by retaining straps or harnesses in order to prevent air leakage.

Flow generators are typically utilized to deliver a breathable gas (i.e., air) to a patient wearing the mask. In CPAP treatment, gas is delivered to the patient's airways at about 2–30 cm $H_2O$ above atmospheric pressure. The flow generator is generally connected to flexible tubing which is secured to the mask worn by the patient. If the flow generator's operation is interrupted as a result of a power outage or other mechanical or electrical failure, there may be a significant build up of carbon dioxide in the mask as the patient's exhaled air is not washed out of outlet vents which are usually contained in the mask. This may present a health problem to the patient.

There have been numerous patents which have addressed some sort of safety valve for gas or air delivery masks. An example of such a patent is U.S. Pat. No. 5,438,981. This patent discloses a counter balanced, rigid valve element which depending on the gas flow, either covers an opening to the ambient air or covers the gas flow airway such that the air or breathing gas is forced out into the ambient air opening. However, this system suffers from being a fairly complicated and expensive system whose correct operation relies on a counter balanced moving part moving relative to its housing. Further, if any condensation from the air gets on or around the balanced valve element, the operation of this valve element can be compromised. This valve is also difficult to clean.

Applicant's international PCT patent application No. PCT/AU97/00849 discloses a valve having a single valve element. However, whilst being simpler than preceding valves of this type, the valve shown in PCT/AU97/00849 still relies on the use of a rigid valve element moving relative to its housing and biased by magnets.

SUMMARY OF THE INVENTION

One aspect of the present invention is directed towards solving or ameliorating one or more of these problems. One aspect of the invention will be described with reference to a full face mask and an anti-asphyxia valve, though other forms of mask and additional components may be used, such as the nasal mask shown in FIG. 4.

It is a further aspect of the present invention to provide an improved valve of simpler construction than those prior art valves discussed above.

Accordingly, in a preferred embodiment, the present invention provides an anti-asphyxia valve adapted to, in use, be disposed between a patient and structure to deliver a breathable gas to the patient. The valve includes a housing having an interior, at least one port to provide fluid communication between the housing interior and atmosphere and at least one flap comprising a first portion adapted for mounting to the housing and a second portion adapted to flex between a first biased open position allowing gas to pass from the housing interior through the at least one port to atmosphere when a difference in gas pressure in the housing interior and atmosphere is below a predetermined operating threshold and a second forced closed position substantially occluding the at least one port when the difference in gas pressure between the housing interior and atmosphere is substantially equal to or above the operating threshold.

The operating threshold can be altered to suit particular applications. For example, a valve suitable for use in adult ventilatory assist therapy has an operating threshold of about 2 cm $H_2O$.

The second portion preferably completely occludes the at least one port in the closed position.

Preferably, the housing may include two housing parts that are releasably engageable with one another. In an embodiment, the housing parts engage by way of bayonet style fittings.

Desirably, the housing may include a gas inlet in the form of a first substantially frusto-conical portion adapted to frictionally engage a flexible conduit in fluid communication with the structure to deliver a breathable gas to the patient and a gas outlet in the form of a second substantially frusto-conical portion adapted to engage a mask or a flexible or rigid conduit in fluid communication with the mask. The frusto-conical portions preferably taper from a smaller distal end to a larger proximal end relative to the housing of the inlet valve.

Desirably also, one of the gas inlet or outlet may include a snap-engageable and detacheable swivel portion adapted to engage the mask or flexible conduit. In a preferred embodiment, the inlet and outlet are respectively provided on one of the two housing parts.

In an embodiment, the housing may include a plurality of ports spaced about the periphery thereof and the second portion of the flap includes a like plurality of flaps. In one preferred form, the housing includes six ports (three pairs of ports) and the second portion of the flap includes three flaps each adapted to close adjacent pairs of the ports. In another embodiment, the second portion of the flap is a single flap which is adapted to occlude all the ports in the second position. The single flap can also include perforations, ribs, pleats or folds or the like.

In one form, the first and second portions are integrally formed. In another form, the first and second portions are initially formed from separate components that are later attached to each other.

The first portion preferably includes a rim adapted to assist in mounting the flap means to the housing. In an embodiment, the rim is an external rim of rectangular cross section which is adapted to engage an internal recess of substantially like cross-section in the housing.

The first portion may also include a cylindrical portion between the rim and the second portion.

The rim and/or the cylindrical portion may also be tapered.

The second portion of the flap preferably terminates in an internal orifice. In a preferred embodiment, the orifice can include a one-way valve adapted to only allow gas flow through the orifice in a direction towards the patient.

In one preferred form, the flap is substantially round in cross-section. In other forms, the cross-section of the flap is full or part elliptical or rectangular or other non-round shapes.

The housing is preferably manufactured from plastics material, for example polycarbonate. The flap assembly is preferably manufactured from a flexible elastomeric material such as a silicone rubber.

In another embodiment, the valve is integral with a mask.

In a further embodiment, the housing is of unitary construction.

These and other aspects of the invention will be described in or apparent from the following detailed description of preferred embodiments.

BRIEF DESCRIPTION OF THE DRAWINGS

Further preferred embodiments of the invention will now be described by way of example only with reference to the accompanying drawings in which.

DETAILED DESCRIPTION OF PREFERRED EMBODIMENTS

Figure 1:
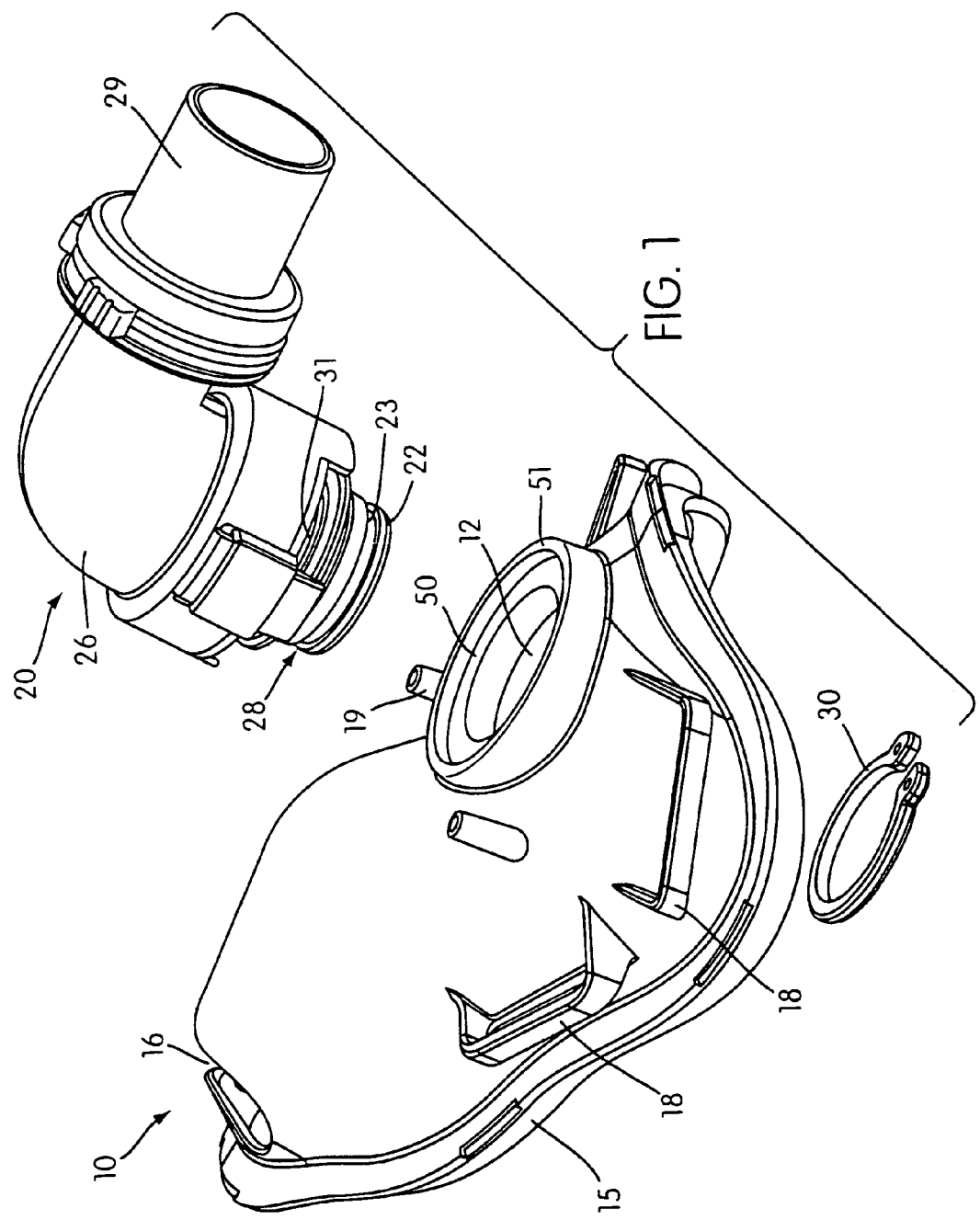
FIG. 1 is a perspective view showing the mask, anti-asphyxia valve housing and conduit connection assembly.

In FIG. 1 a mask frame is shown generally at 10. The mask is designed to be worn on a patient's face and is secured by means of straps (not shown) received by attachment points 18.

A conduit end assembly is shown generally at 20, including an elbow part 26 having at one end thereof a combined vent/connector piece 28. The elbow and vent/connector piece together form a housing for an anti-asphyxia valve (as will be further discussed) or other internal components (not shown). At the other end of the elbow is a detachable swivel tube 29 for connection of the gas delivery conduit (not shown).

The mask 10 includes a circular aperture 12 sized to receive a mating portion 22 of the vent/connector piece 28. The mating portion 22 has an annular groove 23 formed therein that receives a locking means 30 in the form of a C-shaped clip attached after mating to the mask. The clip 30 has an outside diameter greater than the width of the aperture 12 and an inner diameter adapted to ensure a snug fit within the annular groove 23. The clip 30 is resilient and can expand sufficiently to allow the clip to be fitted into and removed from the groove 23. As shown in FIG. 1, the clip 30 is located onto the mating portion 22 on the inside of the mask 10. In this position, the clip 30 is inaccessible while the mask is being worn by a patient. Once the mating portion 22 of the vent/connector piece 28 has been inserted through the aperture 12 and the locking clip placed in the annular groove, the conduit end assembly 20 and the mask 10 cannot be separated without first removing the mask from the patient.

Figure 2:
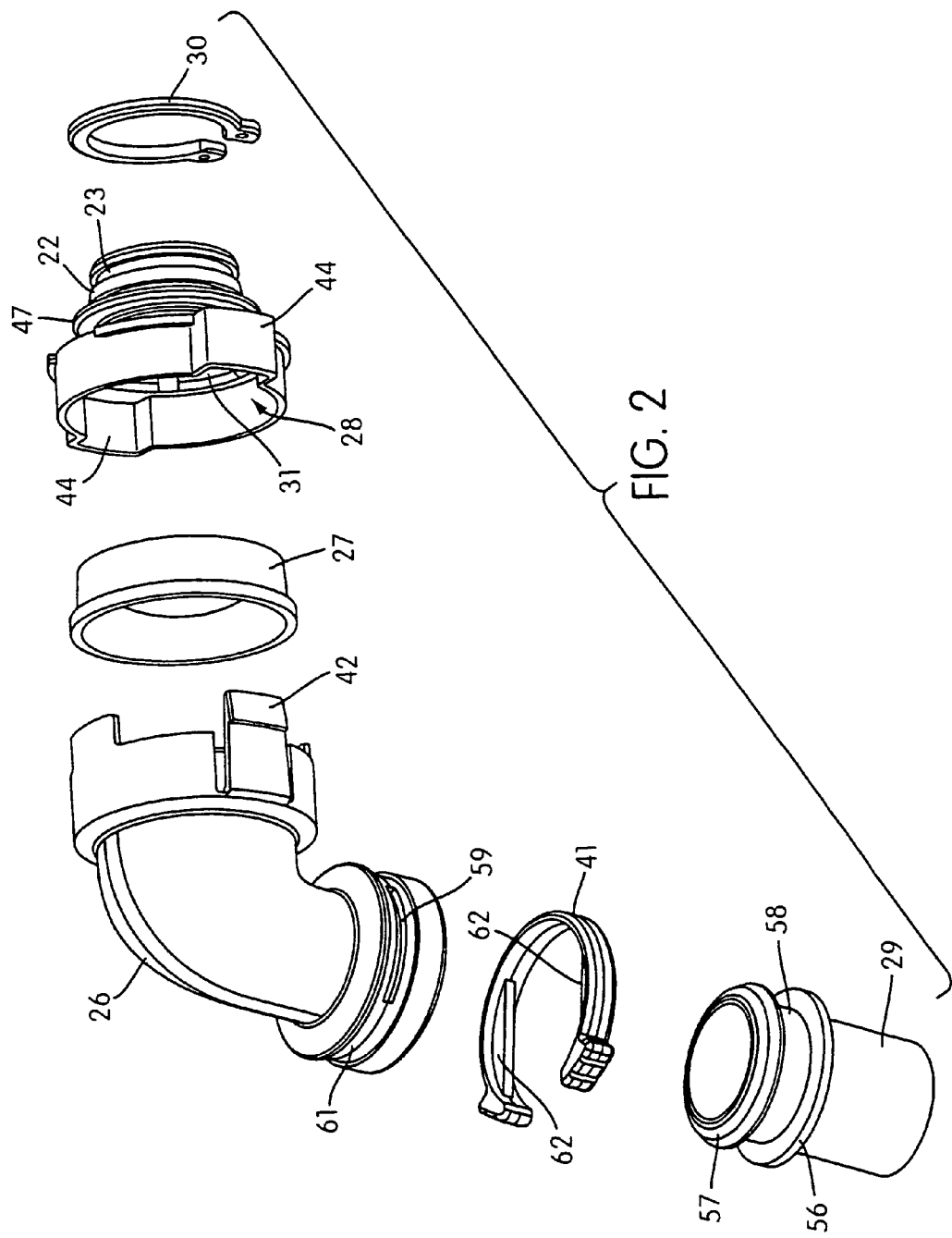
FIG. 2 is an exploded view of the anti-asphyxia valve and conduit connection assembly shown in FIG. 1.

An exploded view of one embodiment of the anti-asphyxia valve and conduit connector assembly is shown in FIG. 2.

As illustrated in FIG. 2, the end of the elbow 26 adjacent the mask 10 is fitted with an anti-asphyxia valve arrangement that provides an air passage to the patient in the event of failure of the gas delivery apparatus, consisting of a valve membrane 27 fitted into the end of elbow 26 and vents 31 in the vent/connector piece 28. During proper operation of the gas delivery system, the valve membrane remains in the orientation shown in FIG. 2, closing off the vents 31. In the event of a drop in pressure below a predetermined level, the valve membrane 27 flips to a reverse orientation, opening the vents 31. The construction and operation of the anti-asphyxia valve is described in more detail in the Applicant's Australian Patent Application No. 65527/99, the contents of which are incorporated herein by reference and described herein.

Resilient detents 42 on the elbow 26 pass through and engage behind slot-forming formations 44 in the vent/connector piece 28 to provide releasable engagement of the two parts.

The vent/connector piece has a collar 47 that abuts a corresponding surface of the mask 10 to limit the distance that the vent/connector piece can be inserted into the mask aperture 12 (FIG. 1). The corresponding surface is an annulus 50 having a protruding rim 51 the outer circumference of which preferably engages the inner surface of the detents 42 on insertion of the mating portion 22 into the aperture 12. This engagement prevents the detents from being pushed radially inwards sufficiently for the detents to disengage from behind the slot-forming formations 44, thus preventing the elbow 26 and vent/connector piece 28 from separating whilst still attached to the mask frame 11, for example during patient treatment. The result of this is that the anti-asphyxia valve arrangement cannot be disassembled without first removing the elbow and vent/connector piece assembly from the mask. However, once disconnected from the mask, the assembly may be readily separated for cleaning and then reassembled.

The other, distal end of elbow 26 has an enlarged diameter portion which receives the swivel tube 29, onto which a flexible gas conduit (not shown) may be fitted. The swivel tube 29 has a pair of flanges 56 and 57 defining an annular groove 58 therebetween. The end of swivel tube 29 is inserted into the elbow 26 until the end flange 57 abuts an inner surface (not shown) within elbow 26. In this position the annular groove 58 is at least partially aligned with an annular groove 61 in the exterior of the elbow, which receives a swivel clip 41.

The swivel clip 41 has an inner diameter only slightly greater than the diameter of the groove 61, to ensure a snug fit within the groove. The clip 41 is resilient to permit sufficient expansion for attachment and removal of the clip from the groove. The groove 61 has slots 59 which receive lugs 62 on the clip. These lugs rotatably engage in the groove 58 between flanges 56 and 57 of the swivel tube. The swivel tube arrangement thus acts as a rotatable coupling between the conduit and the elbow whilst allowing quick attachment and removal of the gas conduit from the elbow regardless of whether the assembly is attached to the mask at the time.

Figure 3:
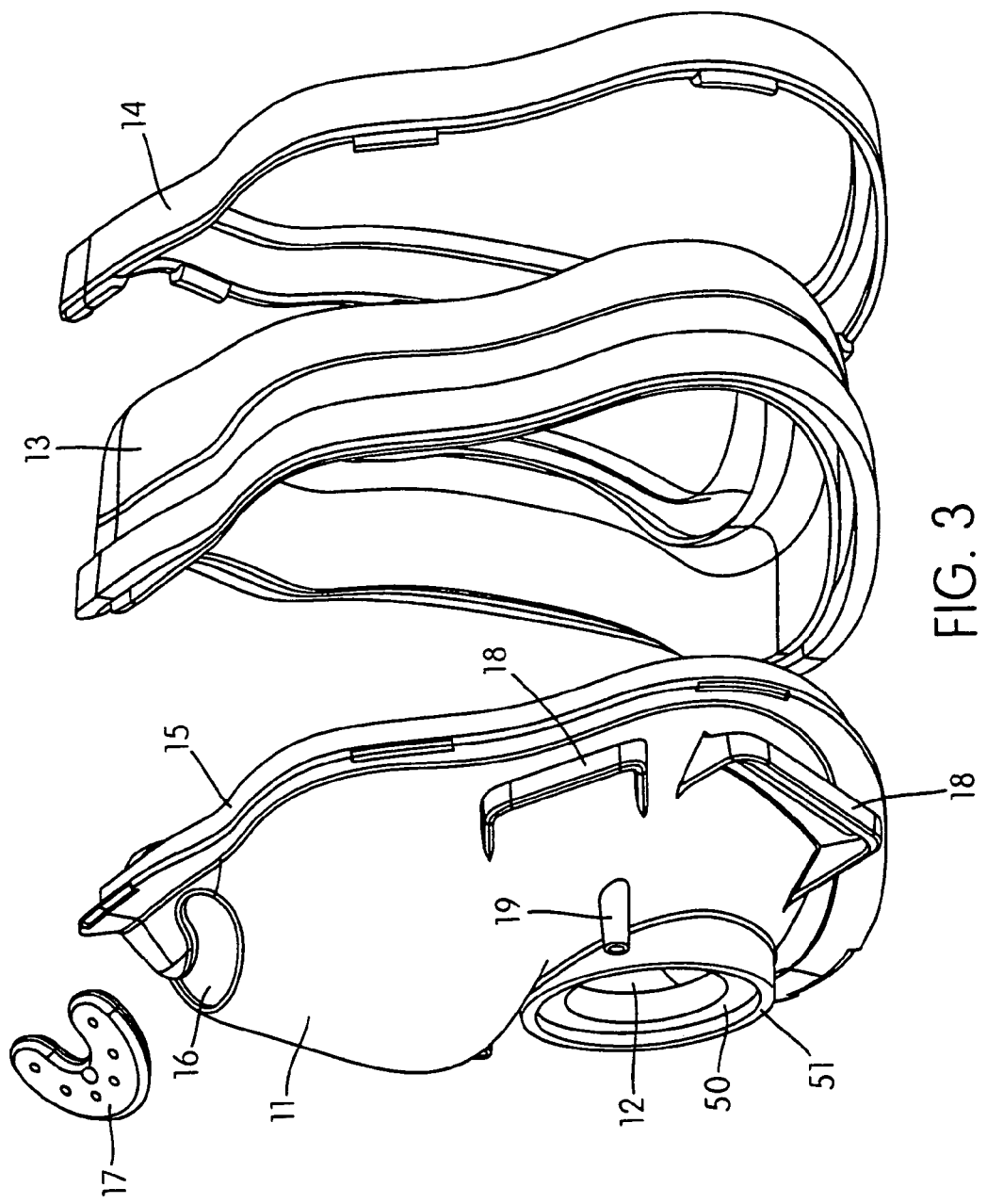
FIG. 3 is an exploded view of the mask assembly shown in FIG. 1.

As shown in FIG. 3, the mask includes a mask frame 11, cushion 13 and cushion clip 14. The cushion is received on a rib 15 extending around the periphery of the mask frame 11. The cushion is held to the rib by the cushion clip 14. The mask frame includes attachment points 18 that receive straps (not shown) for attaching the mask to the patient, an aperture 16 for receiving an air vent 17, and measurement ports 19.

Figure 4:
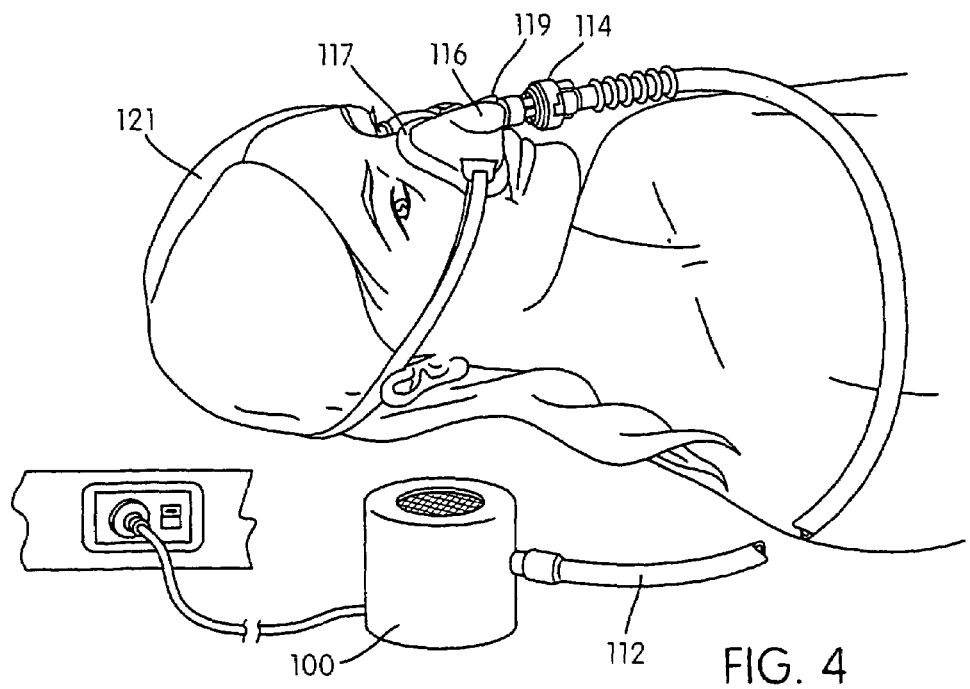
FIG. 4 is a general schematic drawing of a system comprising a flow generator being connected to a valve and mask via tubing in which the mask is connected to a patient.
Figure 5:
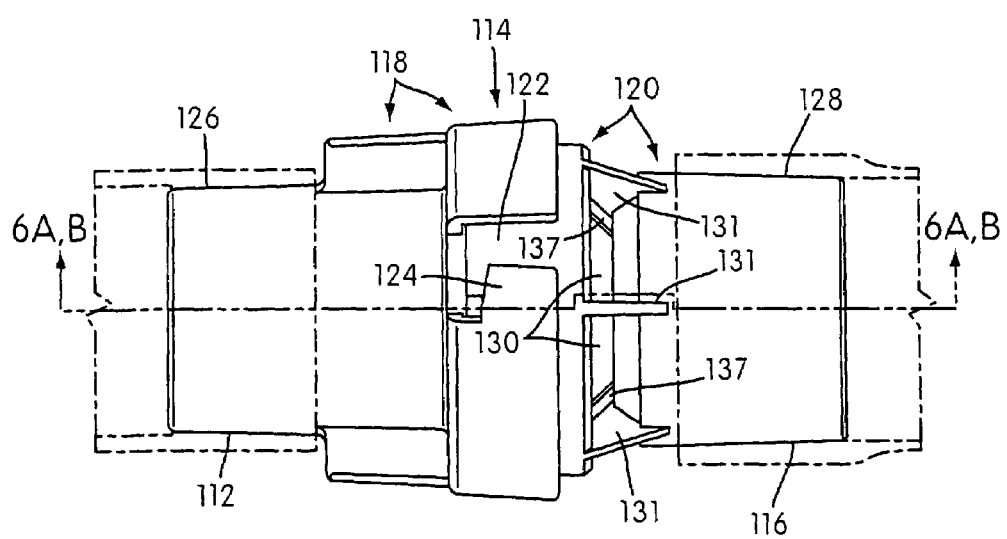
FIG. 5 is a side view of an embodiment of a valve of the present invention.

The details of construction and of the operation of the anti-asphyxia valve will now be described with reference to FIGS. 4–27. As illustrated in FIG. 4, a flow generator 100 having a flexible air flow conduit 112 is secured to an embodiment of a valve 114 which is thereafter connected to a nasal mask 116 of a patient 121. The mask 116 illustrated in FIG. 4 includes a mask cushion 117 and a $CO_2$ gas washout vent 119 and is just one example of numerous types of patient interface. As described above, the mask may be designed to cover the patient's face.

Figure 8:
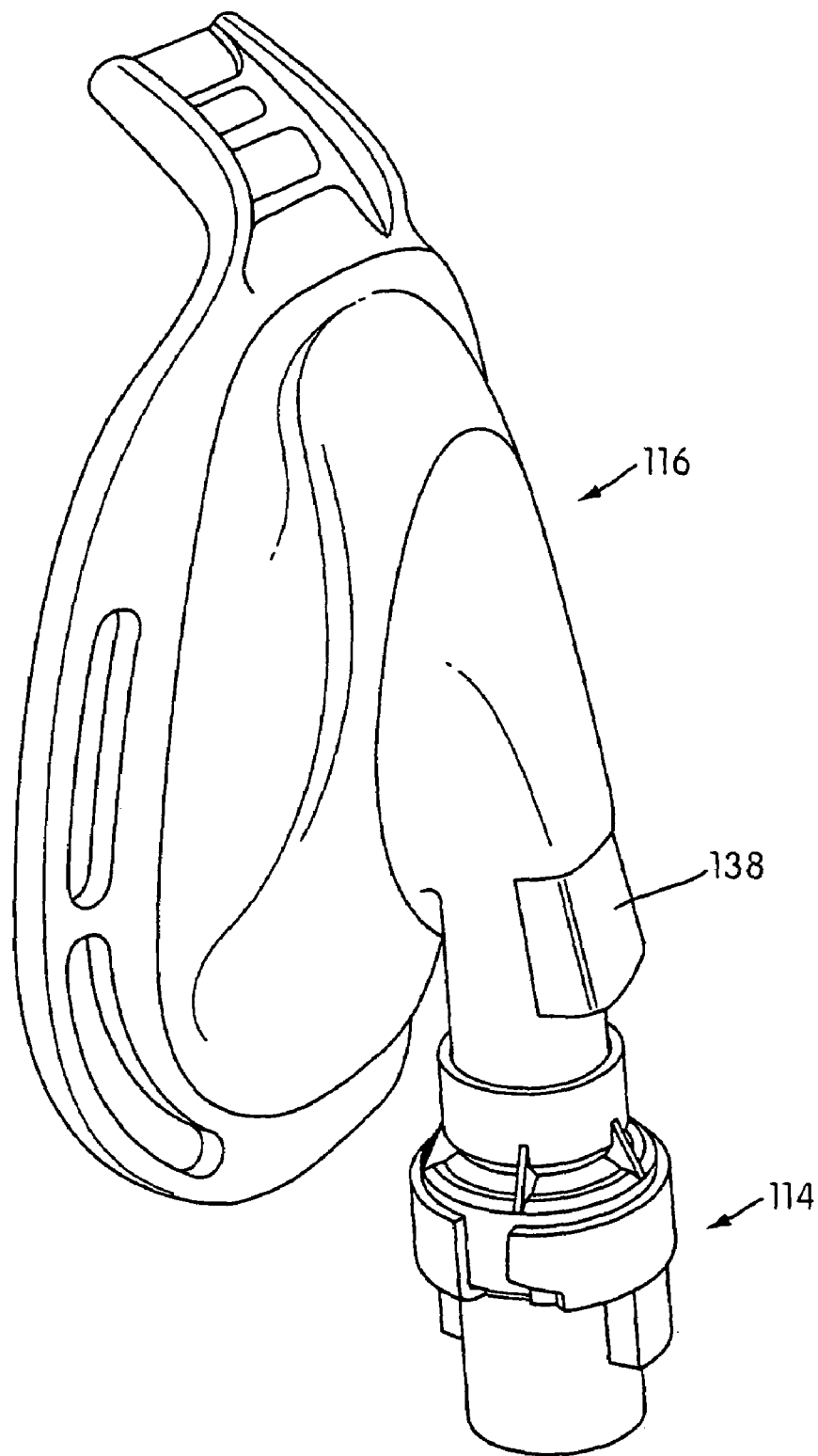
FIG. 8 is a perspective view of an alternative embodiment of the present invention wherein the valve is attached to a mask having a $CO_2$ gas washout vent.
Figure 11:
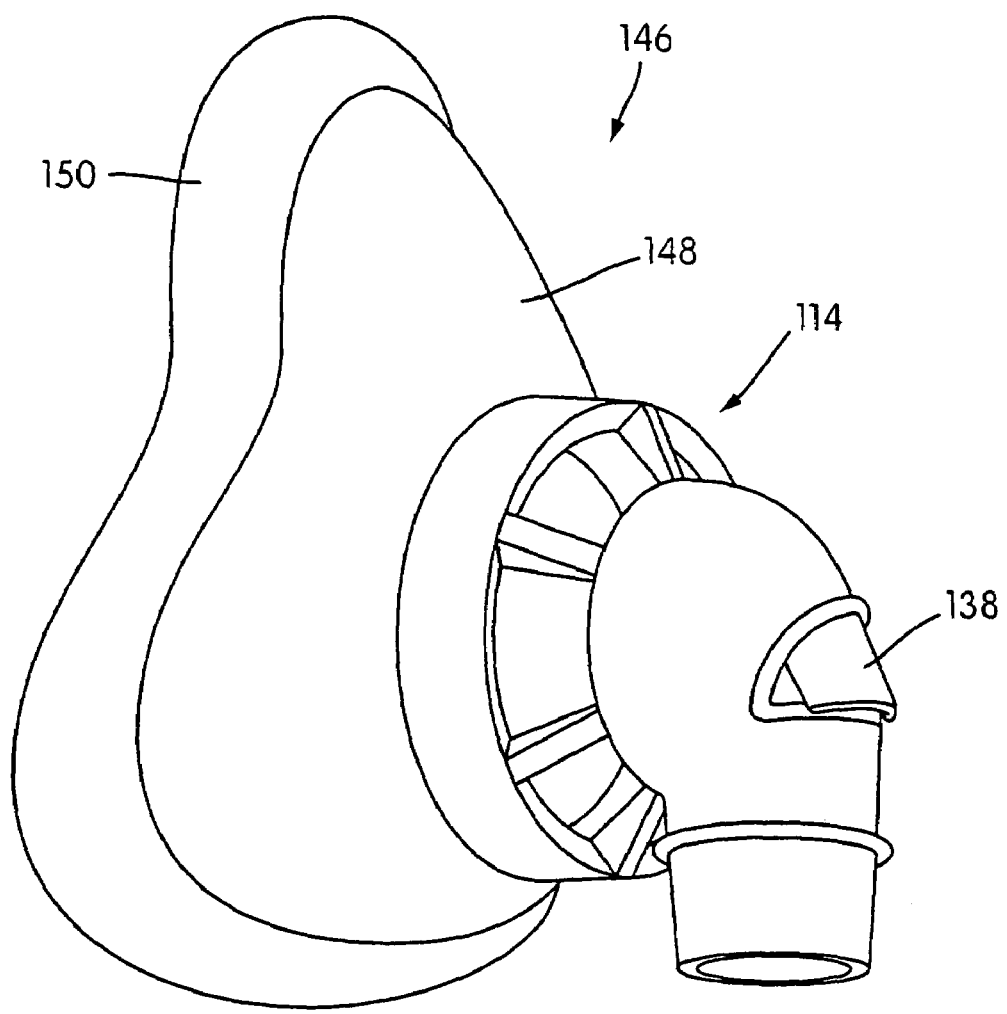
FIG. 11 is a perspective view of another embodiment of the present invention wherein the valve is integral with a mask.

The location of the valve 114 shown in FIG. 4 is just one example of numerous possible locations. The valve 114 could be connected to the mask 116 as shown in FIGS. 4 and 8, or it could be an integral part of the mask 116, as shown in FIG. 11. There could also be two or more valves located on a single system. It is preferred to put the valve 114 as close to the mask 116 as possible, or to make it part of the mask 116.

The flow generator 100 produces a flow of breathable gas, typically air, and can be an electric blower, a controlled bottled gas system, a ventilator, or any other type of device that delivers breathable, therapeutic or anaesthetic gas.

The valve 114 shown in FIGS. 4 to 7 is comprised of two housing parts 118 and 120 which may be locked together by way of respective male and female bayonet fittings 122 and 124. The housing part 118 includes an inlet in the form of frusto-conical portion 126. The housing part 120 includes an outlet in the form of frusto-conical portion 128. The portions 126 and 128 allow push-on assembly and frictional engagement with the gas supply conduit 112 and the mask housing 116 respectively. The housing part 120 includes six peripherally arranged ports 130 each separated by one of six connecting members 131. A flexible flap 132 of generally round cross-section is formed from a silicone rubber and has a central orifice 133. The flap 132 includes a first portion in the form of outer rim 134. The flap 132 is glued, clamped or otherwise attached or mounted to the second housing part 120 at the outer rim 134. The flap 132 includes a second portion in the form of flexible flaps 135.

Figure 6A:
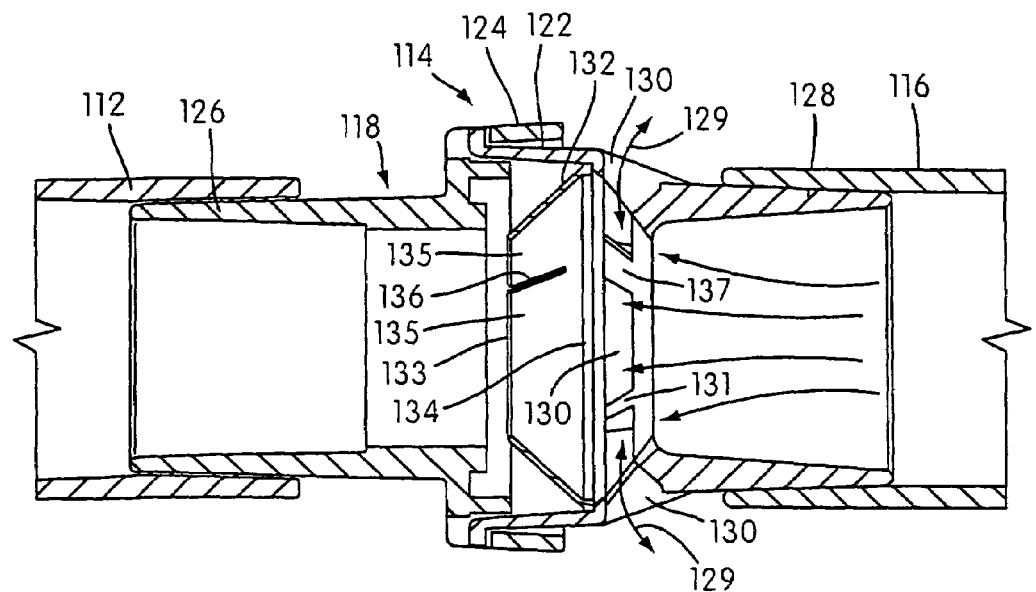
FIG. 6A is a cross-sectional view of FIG. 5 in which the flow generator is not operating.

As shown in FIG. 6A, when the difference in the gas pressure between the housing interior and atmosphere is below a predetermined operating threshold of, for example 2 cm $H_2O$, the flaps 135 are in a relaxed state and inherently biased to an "open" position allowing gas flow from the interior of the housing through the ports 130 and to atmosphere. Accordingly, if the supply of breathable gas falls below the threshold or ceases, the patient 121 is still able to inhale air through the open ports 130 and exhale carbon dioxide out through the open ports 130, as indicated by arrows 129.

Figure 7:
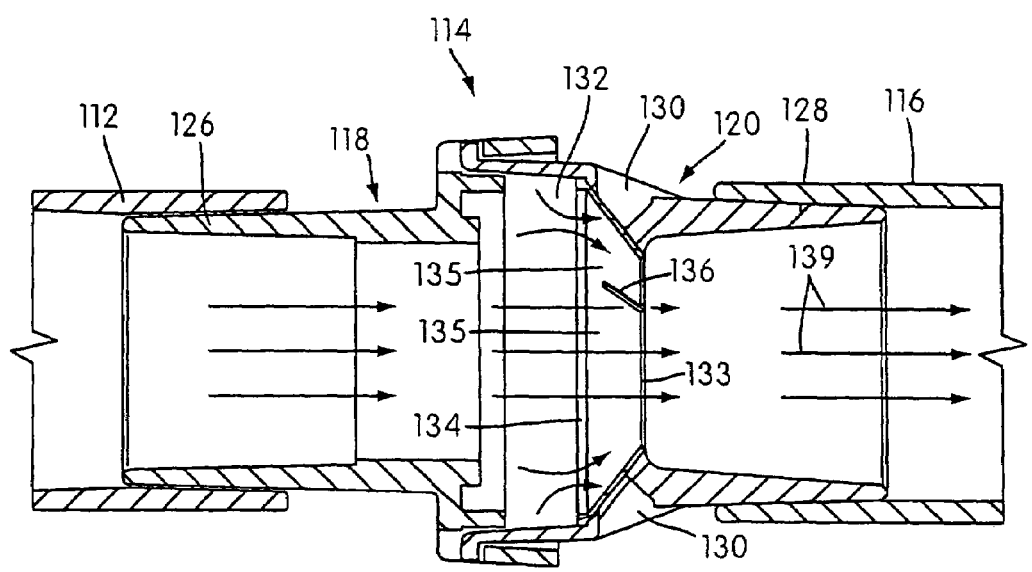
FIG. 7 is a cross-sectional view of the valve of FIG. 5 in which the flow generator is operating and generating a pressure differential above the operating threshold.

When the breathable gas supply commences or resumes and the difference in the gas pressure between the housing interior and atmosphere builds up to equal or above 2 cm $H_2O$ the flaps 135 move to a "closed" position occluding the ports 130 shown in FIG. 7. Thereafter the flaps 135 are maintained closed by the gas pressure in the housing interior being above the predetermined operating threshold. In this closed position all the gas supplied from the flow generator 100 can pass through the orifice 133 of the flap 132 to be delivered to the mask 116 of the patient 121, as indicated by arrows 139.

In the embodiment shown in FIGS. 4 to 7, the flap 132 has three of the flaps 135 which each subtend an angle of approximately 120°. The three flaps 135 are each separated by slits 136 (only one of three slits 136 shown). The slits 136 allow the flaps 135 to flex between the open and closed positions, as shown in FIG. 6A and FIG. 7 respectively, without crinkling or binding. Every second one of the six connecting members 131 includes a flange 137 which abuts adjacent outer edges (adjacent the slits 136) of each of the flaps 135 in the closed position to assist in sealing the ports 130.

Each flap 132 is preferably manufactured by moulding of a single silicone rubber component in the shape shown in FIG. 6A (ie. the open position). The flaps 135 are preferably 0.15 mm thick. The thickness of each of the flaps is adjusted to suit their application and, in particular, the pressure of the operating threshold. If too flimsy, the flaps will distend or crumple across the ports 130 and may not move to return from the closed position at the correct pressure. If too stiff, the flaps will not move to the closed position at the correct pressure.

Testing of a prototype of the valve 114 shown in FIGS. 4 to 7 was conducted with a flow generator connected to the inlet cylindrical portion 126 via an air flow conduit. A mask was connected to the valve 114 at the outlet cylindrical portion 128. The mask cushion seals the mask interior relative to the wearer's face such that the only gas flow from the mask 116 to atmosphere is through the mask gas washout vent.

With this arrangement the flap assembly 132 closed the ports 130 at an approximately 2 cm $H_2O$ pressure difference (operating threshold) between the interior of the valve 114 and atmosphere.

The inherent resilience of the silicone rubber flaps 135 re-opened the ports 130 when the pressure difference (operating threshold) between the interior of the valve 114 and atmosphere fell below approximately 2 cm $H_2O$.

Figure 6B:
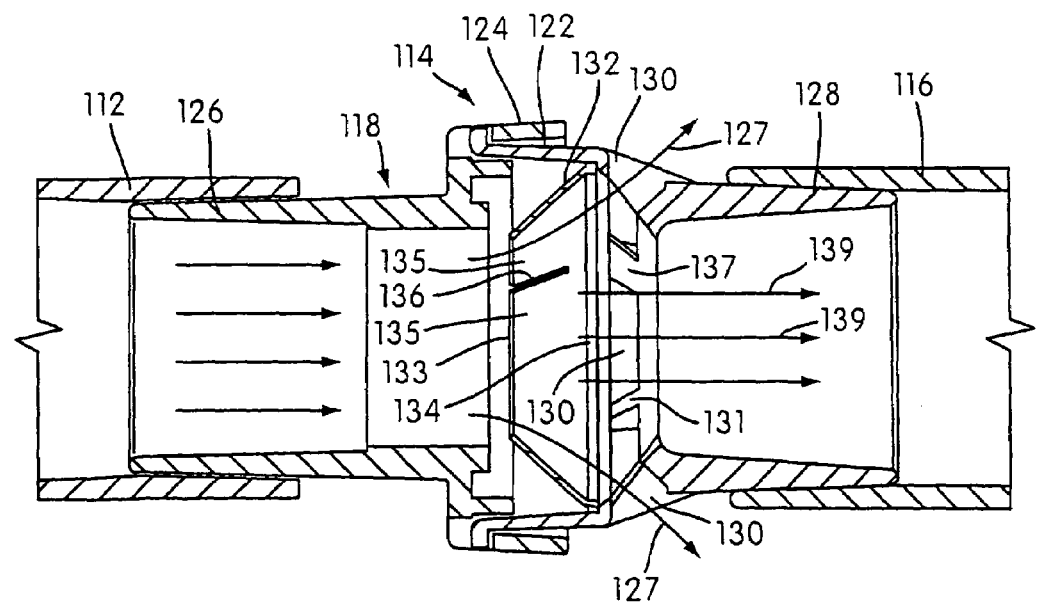
FIG. 6B is a cross-sectional view of FIG. 5 in which the flow generator is operating and generating a pressure differential below the operating threshold.

FIG. 6B shows the flap assembly 132 in the open position when the flow generator is operating but the pressure difference between the valve interior and atmosphere is below the operating threshold. Under these conditions, some of the supplied gas passes through the ports 130 and the remainder passes through the valve outlet 128 to the mask, as indicated by arrows 127 and 139 respectively.

As the flow through the valve outlet 128 is thus less than the supplied flow through the valve inlet 126, a pressure differential is created between the downstream side of the flaps 135 (that side adjacent the valve outlet 128) and the upstream side of the flaps 135 (that side adjacent the valve inlet 126) which forces the flaps 135 to deform against their inherent resilience towards the ports 130 and, ultimately, to the closed position shown in FIG. 7.

When in the closed position shown in FIG. 7, there is no gas flow through the ports 130. Under these conditions, a pressure differential between the valve interior and atmosphere above the operating threshold will maintain the flaps 135 in the closed position.

The inherent resilience of the flaps 135 moves the flaps 135 away from the ports 130 and towards the open position when the pressure difference between the valve interior and atmosphere falls below the operating threshold.

FIG. 8 illustrates another embodiment in which the valve 114 is attached to another type of mask 116 that includes a $CO_2$ gas washout vent 138.

Figure 9:
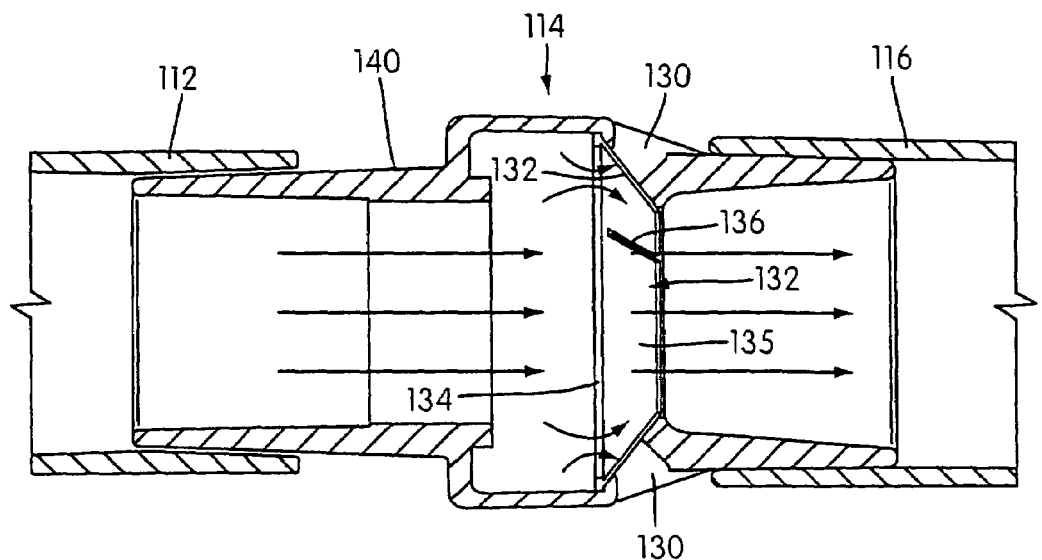
FIG. 9 is a cross-sectional view of a further embodiment of the present invention wherein the valve has a unitary housing.

FIG. 9 illustrates an embodiment of the valve 114 having a unitary housing 140.

Figure 10:
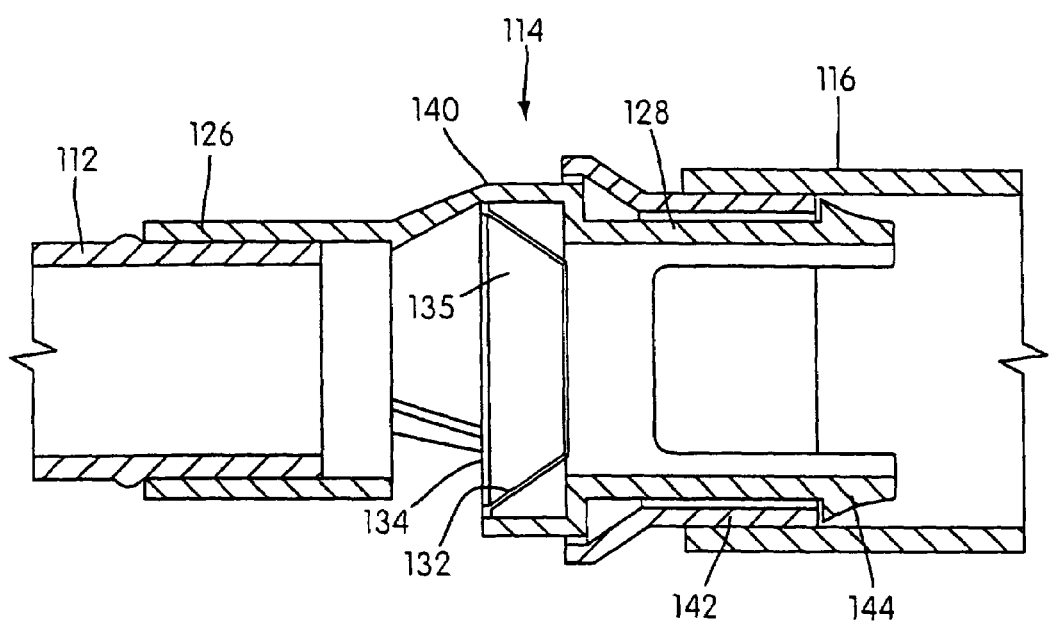
FIG. 10 is a cross-sectional view of a yet further embodiment of the present invention wherein the valve includes a swivel conduit connector.

FIG. 10 illustrates another embodiment of the valve 114 having a unitary housing 140 and a swivel connector 142 that snap-engages with the cylindrical portion 128 over resilient fingers 144. This embodiment obviates the need for a separate swivel connector elsewhere in the gas supply circuit.

In another embodiment (not shown) the swivel connection 142 is used in conjunction with the unitary housing 140.

FIG. 11 illustrates a further embodiment of the valve 114 incorporated into a mask 146 having a mask shell 148 and a mask cushion 150. In this embodiment, the valve 114 is integrally formed with the mask shell 148 thereby obviating the push-on connection between the mask 116 and the valve 114.

Figure 12:
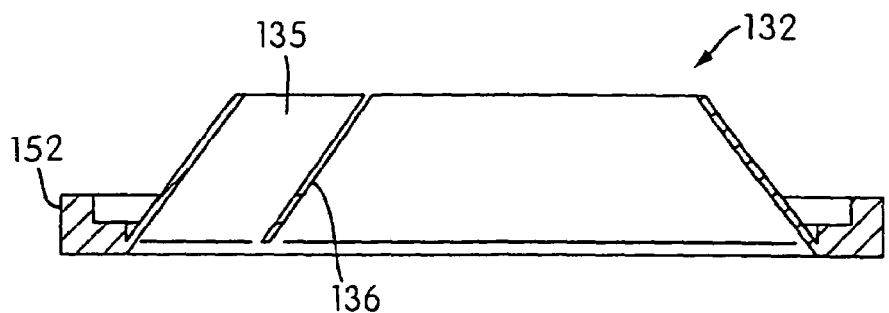
FIG. 12 is a cross-sectional view of an embodiment of a flap.

FIG. 12 shows an embodiment of the flap 132 which includes an external rim 152 of stepped cross section which assists in locating the flap 132 in the housing. The rim 154 is received within a corresponding recess in the housing to facilitate locating and mounting the flap 132 in the housing.

Figure 13:
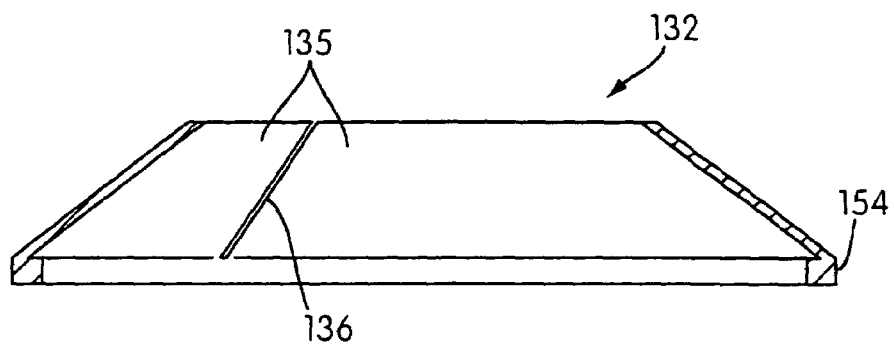
FIG. 13 is a cross-sectional view of another embodiment of a flap.

FIG. 13 shows another embodiment of the flap 132 having an internal rim 154 of rectangular cross section.

Figure 14:
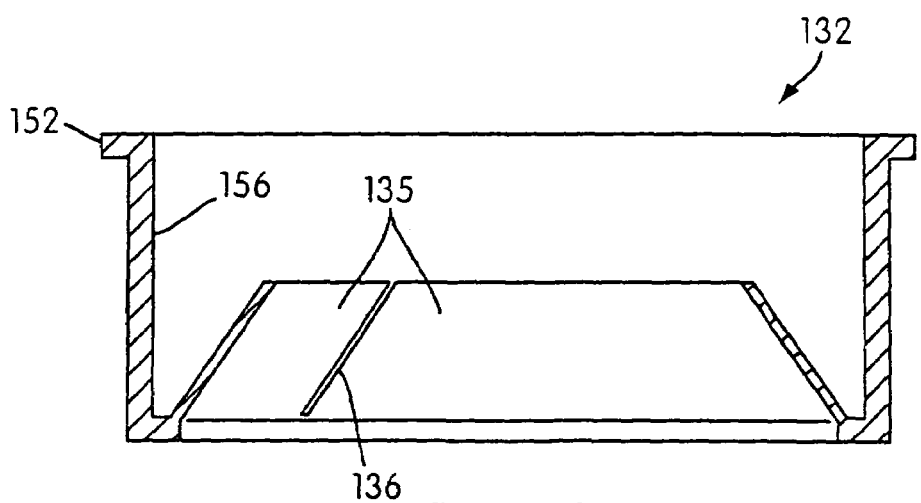
FIG. 14 is a cross-sectional view of yet another embodiment of a flap.
Figure 19:
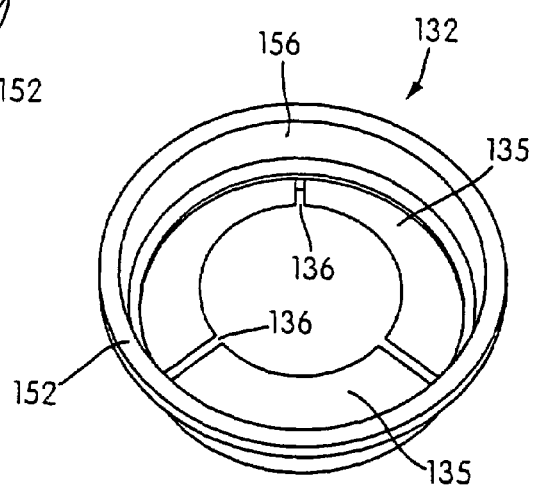
FIG. 19 is a perspective view of the flap shown in FIG. 14.

FIGS. 14 and 19 show yet another embodiment of the flap means 132 having a substantially cylindrical formation 156 between the flaps 135 and the rim 152. The cylindrical formation 156 and the rim 152 facilitate locating the flap 132 with correct orientation in the housing.

Figure 15:
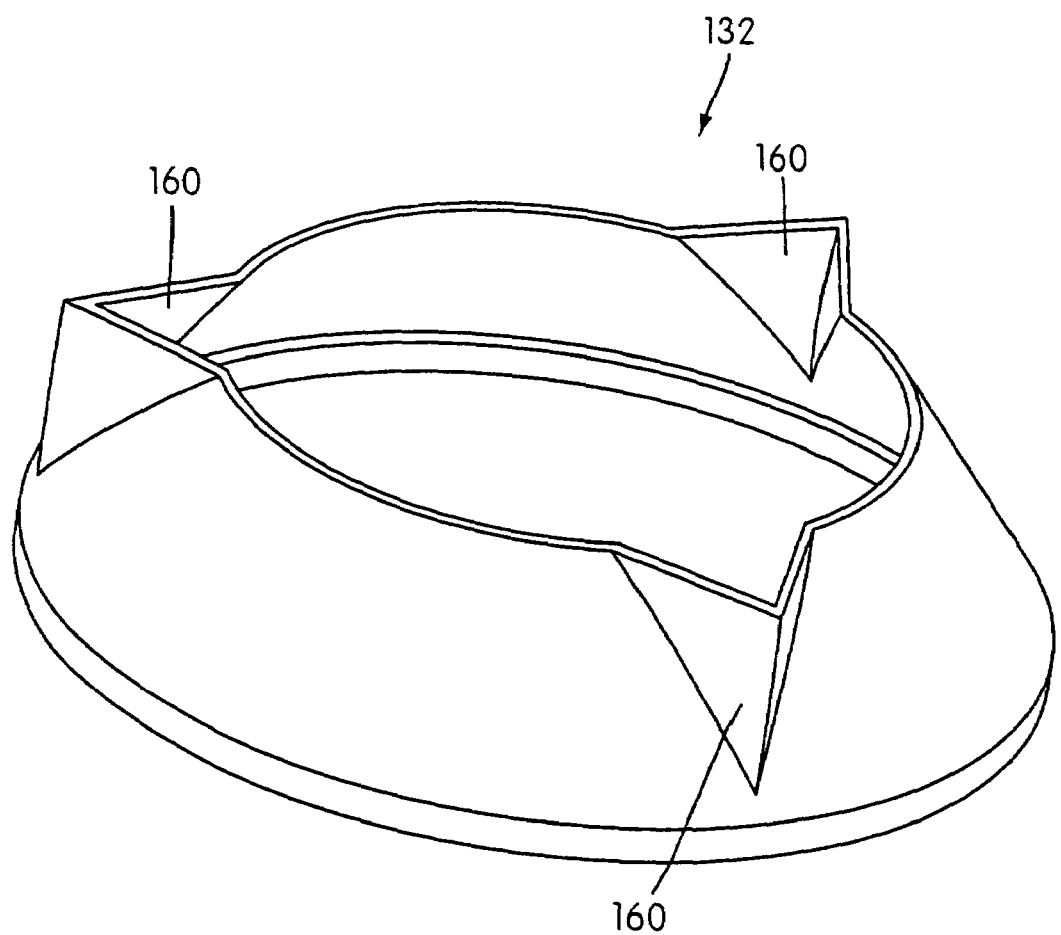
FIG. 15 is a perspective view of a further embodiment of a flap.

FIG. 15 illustrates a further embodiment of the flap 132 which includes a series of pleats or folds 160 which flex to allow movement of the flap 132 between the open and closed positions.

Figure 16:
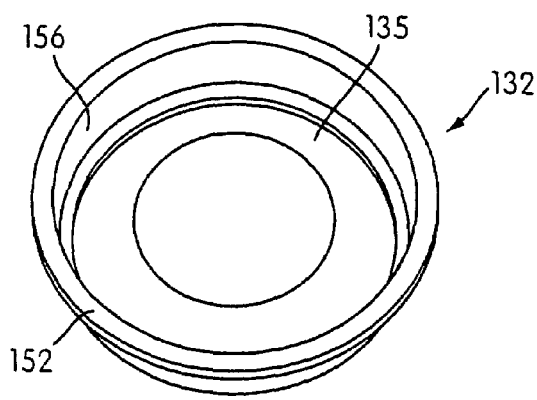
FIG. 16 is a perspective view of a further embodiment of a flap.

FIG. 16 shows another embodiment of the flap 132 similar to that shown in FIG. 14 but without the slits 136. This embodiment thus has only a single flap 135 which distorts when moving between the open and closed positions.

Figure 17:
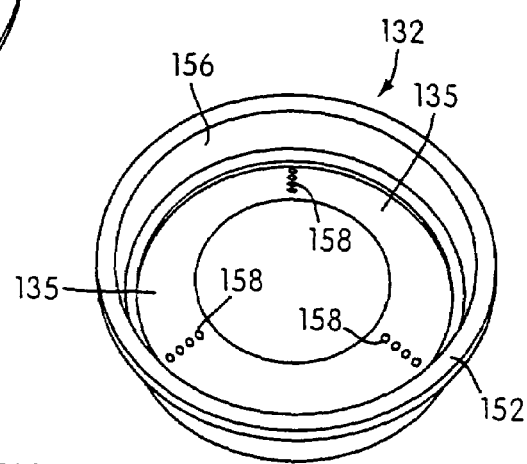
FIG. 17 is a perspective view of a further embodiment of a flap.

FIG. 17 shows an embodiment similar to that of FIG. 16 but including three rows of perforations 158 which provide localised flexability to assist in movement of the flaps 135 between the open and closed positions.

Figure 18:
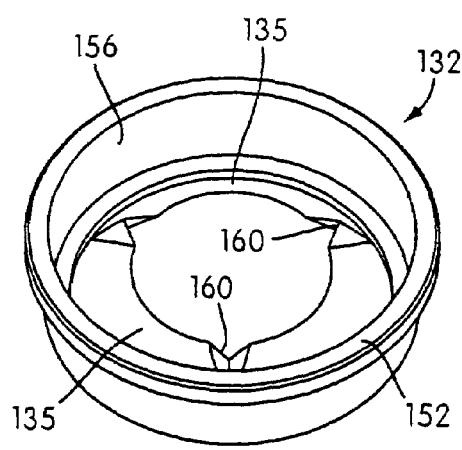
FIG. 18 is a perspective view of a further embodiment of a flap.

FIG. 18 shows an embodiment of a flap 132 that has the cylindrical formation 156 of the embodiment of FIGS. 14 and 19 and the pleats or folds 160 of the embodiment of FIG. 15.

Figure 20:
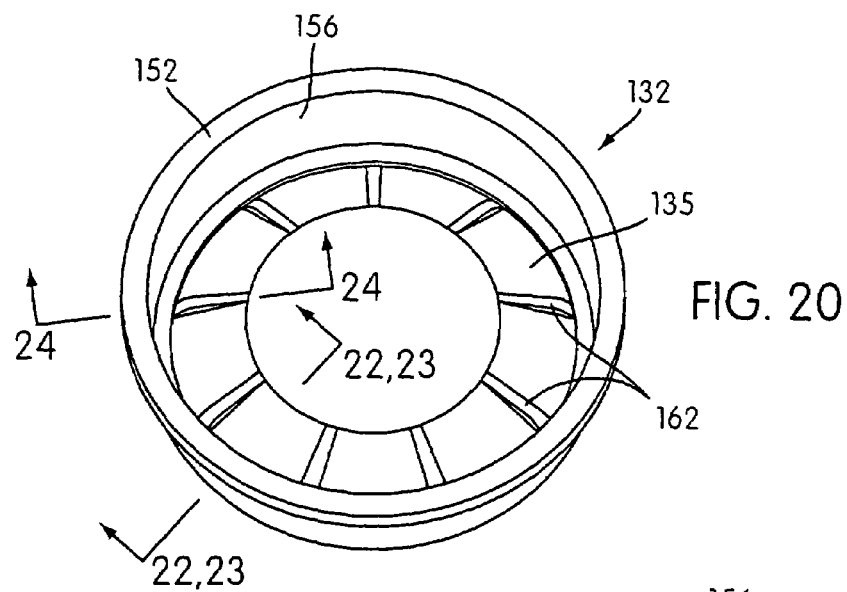
FIG. 20 is a perspective view of a further embodiment of a flap.
Figure 21:
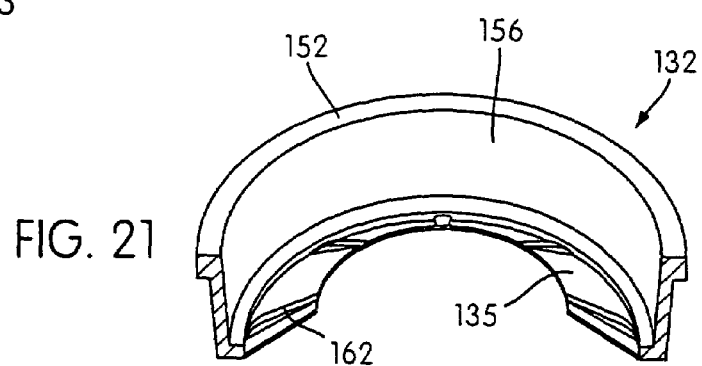
FIG. 21 is a half-cutaway view of the flap shown in FIG. 20.

FIGS. 20 and 21 show a further embodiment of a flap 132 with a single flap 135 that includes a number of radial protuberances' or ribs 162 of greater thickness than the flap 135. In the embodiment shown, the ribs 162 are of equal thickness. In other embodiments (not shown) the ribs are of unequal thickness and, for example, can be thicker on one side for operation in applications where flow is different across the flap such as in a curved or angled conduit or the like.

Figures 22, 23, 24:
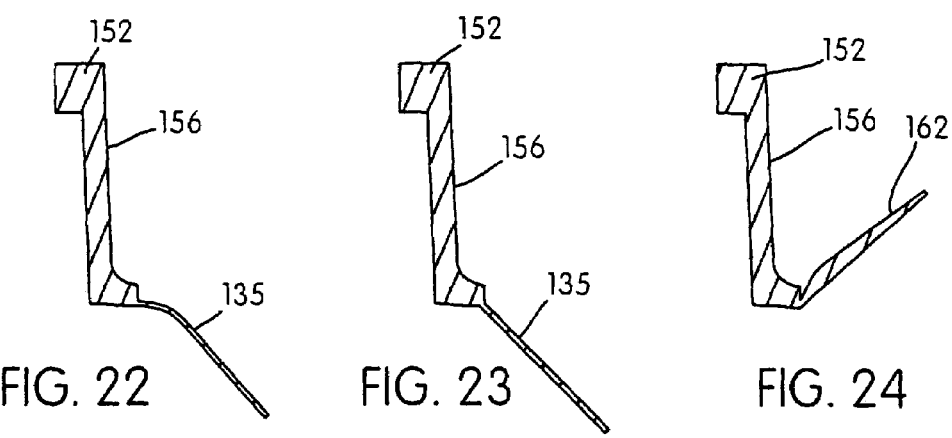
FIG. 22 is a first sectional view of the flap of FIG. 20 along the line 22, 23-22, 23.
FIG. 23 is a second sectional view of the flap of FIG. 20 along the line 22, 23-22, 23.
FIG. 24 is a sectional view of the flap means of FIG. 20 along the line 24—24.

FIGS. 22 and 23 show examples of the cross section the flap 135 can assume in the closed position.

FIG. 24 shows an example of the cross section that the ribs 162 can assume in the open position.

Figure 25:
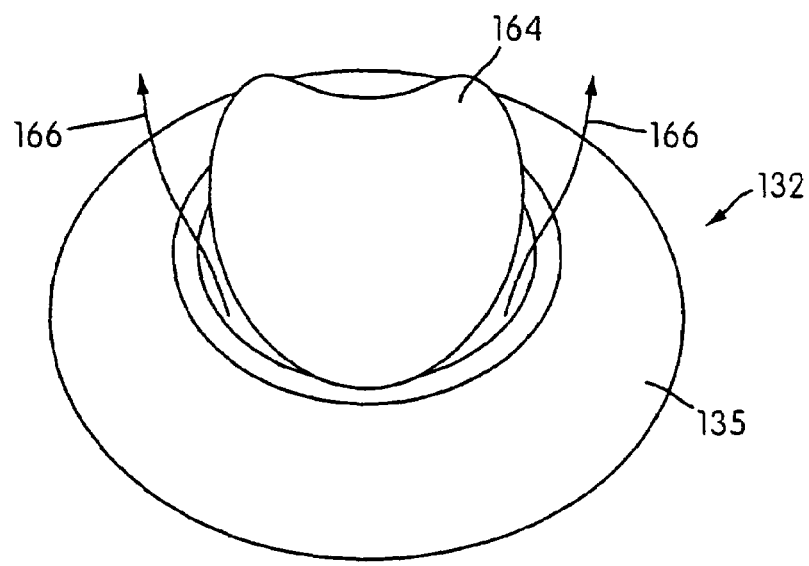
FIG. 25 is a perspetive view of a further embodiment of a flap.
Figure 27:
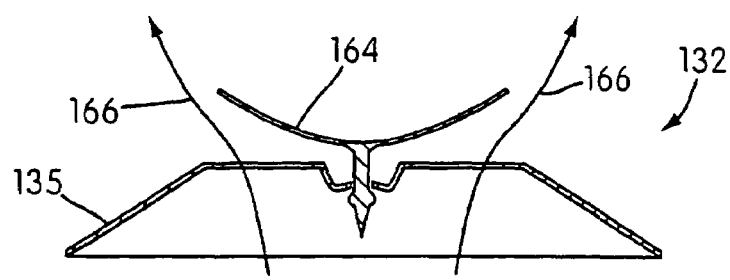
FIG. 27 is a cross-sectional side view of the flap of FIG. 25 in the closed position.

FIGS. 25 and 27 are schematic views of another embodiment of a flap 132 that includes a one-way valve device 164 adapted to only allow gas flow in the direction of the patient. The one-way valve device 164 is known as a non-rebreathe valve.

Figure 26:
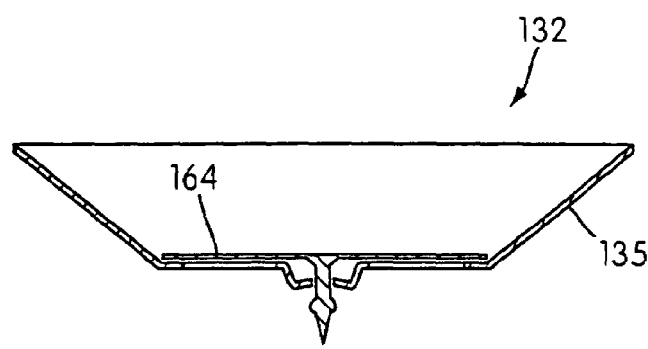
FIG. 26 is a cross-sectional side view of the flap of FIG. 25 in the open position.

FIGS. 25 and 27 show the flap 132 in the closed position and the one-way valve 164 in the open position, thereby allowing gas flow to the patient, as indicated by arrows 166. FIG. 26 shows the flap 132 in the open position and the one-way valve 164 in the closed position, thereby directing all of the gas flow directed through the ports of the valve to atmosphere.

Another embodiment of the invention (not shown) includes a port or series of ports that function as both the flap assembly ports and the mask $CO_2$ gas washout port.

In this embodiment, the ports and the flap assembly are sized so each port is not totally occluded by the flap assembly in the closed position. Accordingly, in the closed position each port is occluded to an extent that it is of a size suitable to function as the mask $CO_2$ gas washout vent. When the pressure differential between the interior of the valve and atmosphere is below the operational threshold, the flap assembly moves to the open position and each port to atmosphere is enlarged to a size suitable to function as the anti-asphyxia port.

One advantage is that the valve can be used with nasal, mouth mask and full face (nose and mouth) mask systems for both adults and infants. In the situation of infants, the airflow is generally less, and thus the force needed to flex the flap assembly into the closed position is lowered accordingly.

The valve according to the present invention can be used for any type of air delivery system, it is preferably used in CPAP applications for the treatment of OSA or NIPPV.

Preferred embodiments of the valve of the present invention have the advantage of being able to operate independent of orientation. That is, although the valve has to be connected in the right direction between the flow generator and the mask, it can be inverted, held sideways, etc. which often occurs during the time when the patient sleeps.

Another advantage of the valve of the present invention is it may have only one moving or flexing part providing consistent operation.

Further, the valve can be disassembled, cleaned and reassembled very easily at home or at a hospital or clinic due to it having less parts.

The valve of the present invention is also very quiet in operation.

Although the invention has been described with reference to specific examples, it will be appreciated by those skilled in the art that the invention may be embodied in many other forms. In particular, a valve of the present invention may be constructed of components which have dimensions, configurations and mechanical properties (including the mechanical properties of the flap assembly) that vary from those of the prototype. Such valves can have operating thresholds different from the prototype valve which achieved a closure at 2 cm $H_2O$. The actual dimensions, configurations and mechanical properties will be chosen to achieve a valve having performance characteristic including operating threshold that will meet the specific needs of the chosen application.

The invention claimed is:

1. A full face mask for a patient comprising:
a frame defining a breathing chamber;
an elbow coupled to the frame, said elbow including a housing having an interior defining a blower side and a patient side, at least one port to provide fluid communication between the housing interior and atmosphere; and an anti-asphyxia valve including at least one flap having a first portion adapted for mounting to the housing and a second portion adapted to flex between a first open position allowing gas to pass from the patient side to the housing interior through the at least one port, and from the blower side through the at least one port, to atmosphere when a difference in gas pressure in the housing interior and atmosphere is below a predetermined operating threshold, and a second forcibly closed position substantially occluding the at least one port when the difference in gas pressure between the housing interior and atmosphere is substantially equal to or above the operating threshold.

2. The mask as claimed in claim 1, wherein the second portion completely occludes the at least one port in the closed position.

3. The mask as claimed in claim 1, wherein the housing includes a gas inlet in the form of a first substantially frusto-conical portion adapted to frictionally engage a flexible conduit in fluid communication with the structure to deliver a breathable gas to the patient and a gas outlet in the form of a second substantially frusto-conical portion adapted to engage a mask or a flexible or rigid conduit in fluid communication with the mask.

4. The mask as claimed in claim 3, wherein the frusto-conical portions taper from a smaller distal end to a larger proximal end relative to the housing of the inlet valve.

5. The mask as claimed in claim 3, wherein one of the gas inlet or gas outlet includes a snap-engageable swivel portion adapted to engage the mask or flexible conduit.

6. The mask as claimed in claim 1, wherein the housing is comprised of two housing parts which are releasably engageable with one another.

7. The mask as claimed in claim 6, wherein the housing parts engage by way of bayonet style fittings.

8. The mask as claimed in claim 6, wherein the inlet and outlet are respectively provided on one of the two housing parts.

9. The mask as claimed in claim 1, wherein the housing is of unitary construction.

10. The mask as claimed in claim 1, wherein the housing includes a plurality of ports spaced about the periphery thereof and the second portion of the flap includes a like plurality of flaps.

11. The mask as claimed in claim 10, wherein the housing includes three pairs of ports and the second portion of the flap includes three flaps each adapted to close adjacent pairs of the ports.

12. The mask as claimed in claim 1, wherein the second portion of the flap is a single flap which is adapted to occlude each said at least one port in the second position.

13. The mask as claimed in claim 12, wherein the single flap includes at least one of perforations, ribs, pleats and folds.

14. The mask as claimed in claim 1, wherein the first and second portions are integrally formed.

15. The mask as claimed in claim 1, wherein the first and second portions are initially formed from separate components that are later attached to each other.

16. The mask as claimed in claim 1, wherein the first portion includes a rim adapted to assist in mounting the flap to the housing.

17. The mask as claimed in claim 16, wherein the rim is an external rim of rectangular cross-section which is adapted to engage an internal recess of substantially similar cross-section in the housing.

18. The mask as claimed in claim 16, wherein the first portion includes a substantially cylindrical portion between the rim and the second portion.

19. The mask as claimed in claim 18, wherein at least one of the rim and the substantially cylindrical portion is tapered.

20. The mask as claimed in claim 1, wherein the second portion of the flap preferably terminates in an internal orifice.

21. The mask as claimed in claim 20, wherein the orifice includes a one-way valve adapted to only allow gas flow through the orifice in a direction towards the patient.

22. A full face mask for a patient comprising:
a frame defining a breathing chamber;
an elbow coupled to the frame, said elbow including a housing having an interior defining a blower side and a patient side, at least one port to provide fluid communication between the housing interior and atmosphere; and
an anti-asphyxia valve having a flap, wherein the flap is substantially round in cross-section.

23. The mask as claimed in claim 22, wherein the housing is manufactured from plastics material.

24. The mask as claimed in claim 23, wherein the plastics material is polycarbonate.

25. The mask as claimed in claim 22, wherein the flap is manufactured from a flexible elastomeric material.

26. The mask as claimed in claim 25, wherein the elastomeric material is silicone rubber.

27. The mask as claimed in claim 22, wherein the operating threshold is about 2 cm $H_2O$.

28. The mask as claimed in claim 22, wherein a first portion of the at least one flap is fixed relative to the housing in a first open position and a second forcibly closed position.

29. The mask as claimed in claim 22, wherein the flap has one end mounted to the housing.

30. A full face mask for a patient comprising:
a frame defining a breathing chamber;
an elbow coupled to the frame, said elbow including a housing having an interior defining a blower side and a patient side, at least one port to provide fluid communication between the housing interior and atmosphere; and
an anti-asphyxia valve having a substantially conic section, said valve having at least one flap.

31. The mask as claimed in claim 30, wherein the at least one flap is adapted to evert between a first position to open the port and a second forcibly closed position to close the port.

32. The mask as claimed in claim 30, wherein the flap has one end mounted to the housing.

* * * * *